United States Patent [19]

Rosenbloom et al.

[11] Patent Number: 5,221,257
[45] Date of Patent: Jun. 22, 1993

[54] APPARATUS AND METHOD FOR FEMORAL VENOUS CANNULATION

[75] Inventors: Michael Rosenbloom; Alan D. Muskett, both of St. Louis, Mo.; Robert J. Todd, Salt Lake City, Utah

[73] Assignee: Research Industries Corporation, Midvale, Utah

[21] Appl. No.: 692,095

[22] Filed: Apr. 26, 1991

[51] Int. Cl.⁵ ............................................. A61M 31/00
[52] U.S. Cl. ...................................... 604/53; 604/264; 604/280; 128/772
[58] Field of Search ........................................ 604/4–6, 604/49, 52–53, 93, 264, 270, 280, 282, 265; 128/657–658, 772

[56] References Cited

U.S. PATENT DOCUMENTS

| | | | |
|---|---|---|---|
| 4,129,129 | 12/1978 | Amrine | 128/214 R |
| 4,173,981 | 11/1979 | Mortensen | 604/282 |
| 4,195,637 | 4/1980 | Grüntzig et al. | 604/53 |
| 4,299,226 | 11/1981 | Banka | 604/52 |
| 4,402,684 | 9/1983 | Jessup | 604/264 |
| 4,413,989 | 11/1983 | Schjeldahl et al. | 604/96 |
| 4,456,000 | 6/1984 | Schjeldahl et al. | 606/194 X |
| 4,552,554 | 11/1985 | Gould et al. | 604/51 |
| 4,573,476 | 3/1986 | Ruiz | 128/658 |
| 4,639,252 | 1/1987 | Kelly et al. | 604/282 |
| 4,740,195 | 4/1988 | Lanciano | 604/95 |
| 4,820,349 | 4/1989 | Saab | 604/194 |
| 5,011,469 | 4/1991 | Buckberg et al. | 604/4 |
| 5,049,138 | 9/1991 | Chevalier et al. | 604/265 |

OTHER PUBLICATIONS

Paper entitled "Left Thoracotomy for Reoperative Coronary Artery Bypass Procedures," The Annals of Thoracic Surgery, vol. 40, No. 1, Jul. 1985, Ross M. Ungerleider et al.
Product Sheet, "Long Venous and Arterial VAD Perfusion Cannulae," Research Medical, Inc.
Product Sheet, "FEM-FLEX ™ Femoral Cannulation Set," Research Medical, Inc.

*Primary Examiner*—C. Fred Rosenbaum
*Assistant Examiner*—C. Maglione
*Attorney, Agent, or Firm*—Madson & Metcalf

[57] ABSTRACT

A guide for assisting in the cannulation of a patient comprising a flexible, tubular body having a hollow interior, a proximate end, and a distal end. The proximate end has an opening in communication with the hollow interior of the tubular body, and the distal end has a rounded, reinforced tip with a passageway therethrough which is in communication with the hollow interior. The guide is inserted and advanced to a position desired by the surgeon within a vein or artery, and then a cannula is threaded over the guide and advanced to the desired position before the guide is removed from the patient. The guide may be used in conjunction with a guide wire and/or a dilator.

14 Claims, 3 Drawing Sheets

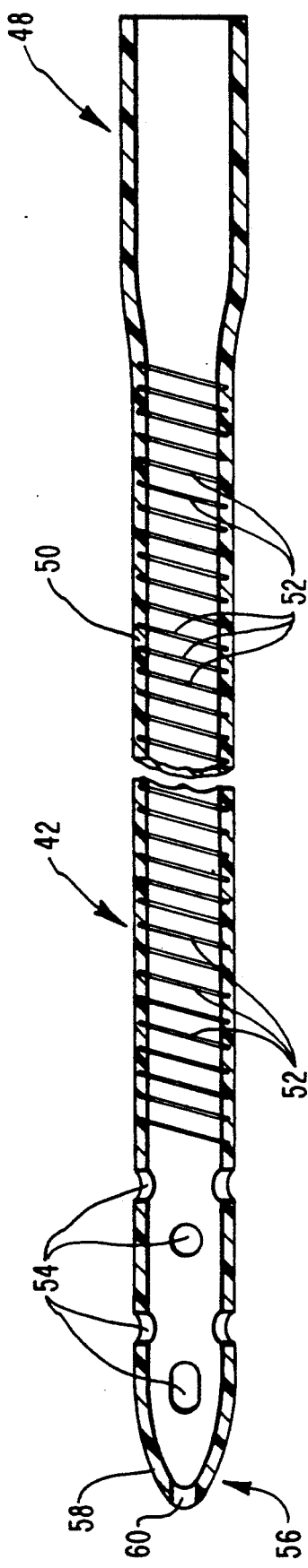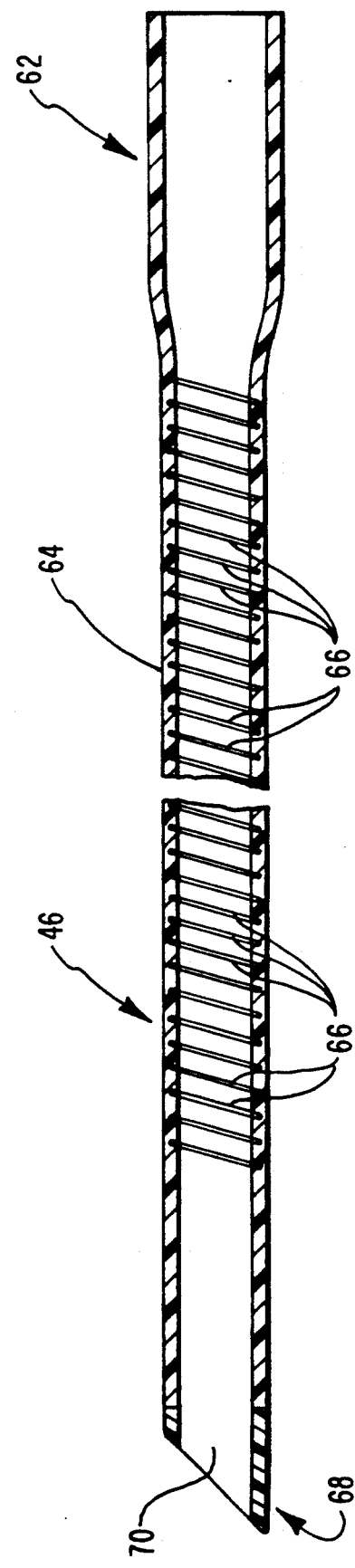

APPARATUS AND METHOD FOR FEMORAL VENOUS CANNULATION

FIELD OF THE INVENTION

The present invention relates to catheters used in draining venous blood for treatment in extracorporeal life support equipment during surgical procedures requiring cardiopulmonary bypass, and more particularly to a simplified apparatus and method for femoral venous cannulation.

BACKGROUND OF THE INVENTION

In a variety of surgical procedures, it has become routine to utilize extracorporeal cardiopulmonary bypass in order to mechanically perform the functions normally conducted by the heart and lungs. Venous blood depleted in oxygen and rich in carbon dioxide is mechanically removed from the patient and pumped to oxygenating apparatus in order to oxygenate the blood and remove excess carbon dioxide. The blood is then returned to the patient's arterial system.

It is critical that adequate volumes of blood be drained from the patient during cardiopulmonary bypass so that the extracorporeal life support equipment can meet the patient's needs for oxygen and carbon dioxide removal. Serious tissue damage can result if insufficient quantities of oxygen are supplied to the patient. Further, acidosis may result from inadequate removal of carbon dioxide.

Various techniques and catheter designs have been used during extracorporeal treatment to provide venous drainage. In the past, femoral venous cannulation has been used as a backup procedure to other preferred procedures. In situations when preferred procedures for venous cannulation are especially difficult, femoral venous cannulation may be used. For example, venous cannulae may be especially difficult to pass when the patient is in the left thoracotomy position as for the repair of thoracic aneurysms, reoperative coronary artery bypass grafting, or left lung transplantation.

Consequently, there has been increasing use of femoral-femoral cardiopulmonary bypass in certain situations, emphasizing the need to be able to reliably obtain adequate venous drainage in a safe and rapid manner.

Heretofore, however, there have been serious drawbacks to femoral venous cannulation. Patient positioning and local anatomy may make passage of large venous cannulae difficult, if not impossible. In addition, forceful advancement of rigid cannula into the femoral or iliac veins may lead to disastrous complications such as vessel laceration.

Adequate venous drainage for cardiopulmonary bypass is often difficult to achieve via the femoral veins unless the venous cannula is positioned near the right atrium of the heart. This requires the cannula to travel a long distance from the venotomy to the right atrium of the heart. Frequently, guide wires that are used to direct the venous cannula into position are too thin and flexible to guide the cannula into the optimal position. Additionally, there is always the danger that the guide wire will lacerate the vein. An additional problem is that the passage of large cannulae through femoral and iliac veins is sometimes difficult because of the anatomy of the patient's venous system, previous surgery, calcified arteries and/or the sacral promontory.

Thus, it would be a substantial contribution to venous cannulation if an improved apparatus and method for effecting rapid femoral cannulation could be provided. It would be a further advance in the art if the apparatus could also be used to effect femoral arterial cannulation. The present invention provides such an apparatus and method.

OBJECTS AND BRIEF SUMMARY OF THE INVENTION

In view of the foregoing needs and problems experienced during extracorporeal cardiopulmonary bypass and the drawbacks of femoral venous cannulation, it is a primary object of the present invention to provide a device for use in effecting rapid femoral cannulation without causing unnecessary damage.

It is another object of the present invention to provide an apparatus that simplifies the insertion of a venous catheter near the right atrium of the heart.

A further object of the present invention is to provide a method for femoral venous cannulation that can be used as a first system for venous drainage during extracorporeal cardiopulmonary bypass surgery.

Another object of the present invention is to provide a soft atraumatic guide for insertion of a large diameter catheter, either venous or arterial, into a patient.

Still another object of the present invention is to provide a guide that can be used either with or without a guide wire to position a catheter within a patient.

Yet another object of the present invention is to provide a guide that can be used either with or without a dilator.

The foregoing objects are accomplished by an apparatus of the present invention having an elongate tubular body and a rounded distal end so configured for use in a simple method for rapidly achieving femoral venous cannulation.

In one preferred embodiment of the present invention the guide comprises an elongate tubular body of relatively small diameter. The proximate end of the tubular body has an opening that extends the full length of the tubular body to and through the distal end of the tubular body. The distal end is rounded and reinforced. The opening is of sufficient diameter that a guide wire can pass therethrough readily. The guide is constructed of a soft, but structurally stable, material that is flexible but retains its basic shape.

The guide of the present invention may be used to assist in the insertion of either a venous catheter or an arterial catheter. When it is desirable, the guide can be used in conjunction with a guide wire and/or with a dilator.

By utilizing the guide of the present invention, a simple method for proper placement of femoral venous cannulae is provided. The femoral vessels are exposed surgically in a routine manner. A venotomy is made and the soft guide of the present invention is advanced via the common femoral vein. Since the guide is soft and flexible, it is manipulated easily into the inferior vena cava and then into the right atrium, if needed. A standard venous cannula having a slightly enlarged tip opening passes over the guide. The venous cannula is then advanced over the guide and into the desired position.

In the event that there is difficulty in advancing the guide of the present invention into the venous system of the patient, a long guide wire can be advanced through the femoral venotomy and the guide can then be passed easily over the guide wire into position for the insertion of the larger venous cannula. Typically, because guide wires are too thin and flexible, the guide wire alone is incapable of guiding rapidly the venous cannula into the desired position.

These and other objects and features of the present invention will become more fully apparent through the following description and appended claims taken in conjunction with the accompanying drawings.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 5 is a longitudinal sectional view of a venous cannula with a slightly enlarged opening in its tip for use in conjunction with the guide of the present invention; and FIG. 6 is a longitudinal sectional view of an arterial cannula of a type that can be used with the guide of the present invention to effect arterial cannulation.

DETAILED DESCRIPTION OF THE PREFERRED EMBODIMENTS

Figures 1, 2:
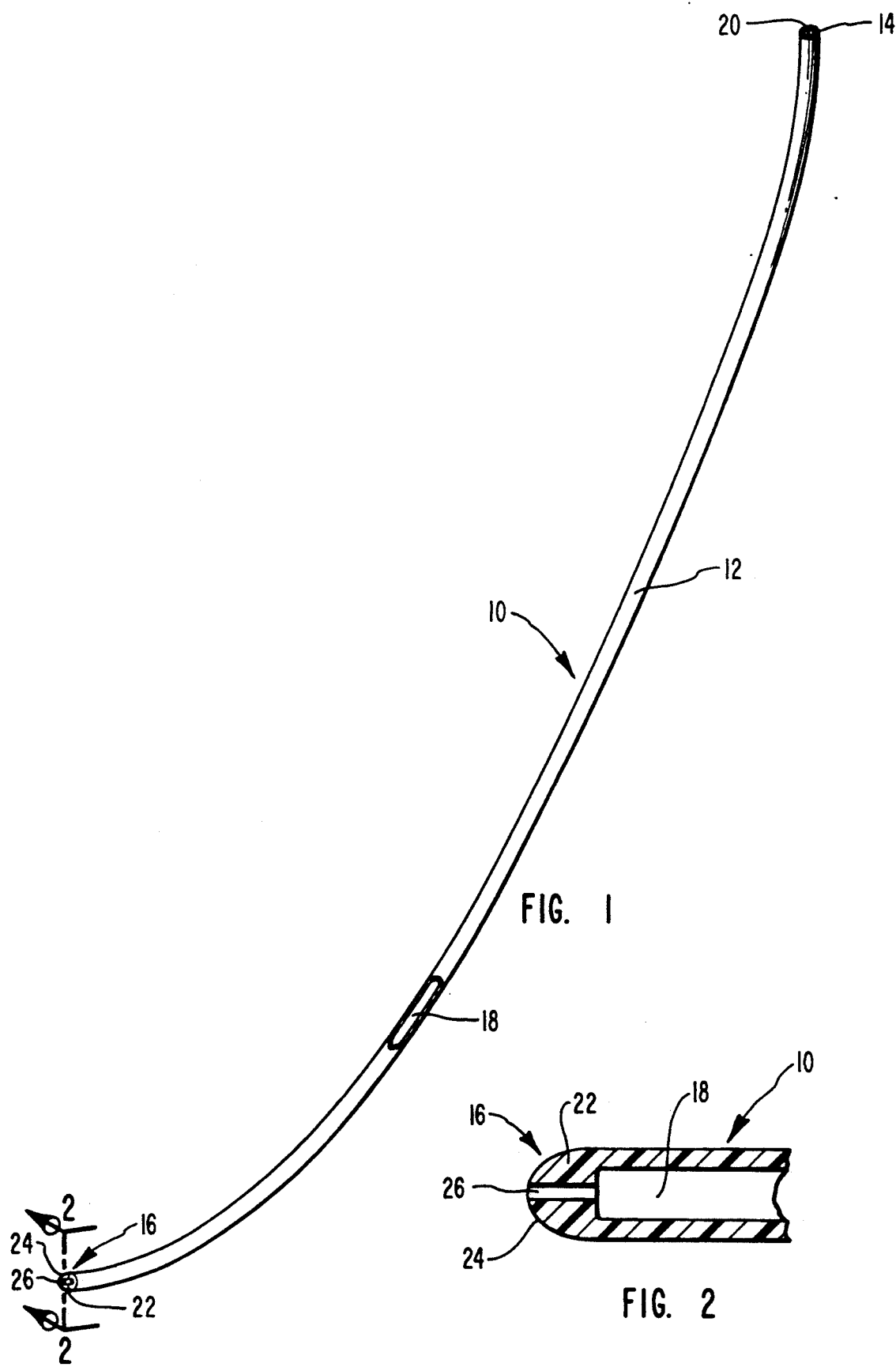
FIG. 1 is a perspective view of the guide of the present invention with a portion cut away to illustrate the hollow interior of the guide.
FIG. 2 is an enlarged, longitudinal sectional view of the distal end of the guide of the present invention along line 2—2 of FIG. 1.

Referring now specifically to the drawings, wherein like numerals indicate like parts throughout, the guide of the present invention is generally designated at 10. As best shown in FIG. 1, guide 10 comprises a hollow, tubular body 12, a proximate end 14 and distal end 16.

Tubular body 12 has a hollow interior 18 and is long enough to extend from a femoral venotomy into the right atrium of the heart with ample protruding from the venotomy for handling by the surgeon. The hollow interior 18 extends the full length of the tubular body 12. The diameter of the hollow interior 18 is sufficient to freely accept passage therethrough of a conventional guide wire. It is preferred that the tubular body 12 have an outermost diameter of approximately 14 French and be constructed of a flexible, yet form retaining material such as PVC. Although larger or smaller diameters (e.g., a range from 10 to 20 French) and other materials may be used, the diameter and material recited above are preferred because optimal efficiency of the guide is achieved without weakening the venous cannula or endangering the interior venous wall. Additionally, if a fluoroscopy indicator such as a barium or bismuth stripe is applied to the guide 10, the guide 10 and its relative position within a patient will be visible by fluoroscopy.

The proximate end 14 has an opening 20 which communicates with the hollow interior 18 of the tubular body 12 so that a conventional guide wire may pass through the opening 20 and into the hollow interior 18 easily without binding.

Referring now to FIG. 2, it can be seen that distal end 16 comprises a reinforced tip 22 having a rounded leading surface 24 and a passageway 26. The reinforced tip 22 facilitates the insertion and advancement of the guide 10 through a patient's venous or arterial system because it provides rigidity at the leading portion of the guide. In combination with the rounded leading surface 24, the reinforced tip 22 significantly reduces the possibility that the guide 10 will snag or hang up on the interior vessel wall or that the guide will kink or resist insertion or advancement. Passageway 26, like opening 20, communicates with hollow interior 18. However, it is preferred that passageway 26 have a diameter that is only slightly larger than and more closely approximates the diameter of conventional guide wires. In this manner, a guide wire that is threaded into the opening 20 and through the hollow interior 18 and then through passageway 26 receives additional lateral support from the reinforced tip 22. Also, a guide wire so threaded is centered within the vessel, thereby reducing the possibility that the guide wire will snag or hang up on the interior wall of the vessel.

Although it is preferred that passageway 26 have a diameter that is only slightly larger than the diameter of conventional guide wires, it should be understood that a larger diameter passageway 26 may be used without departing significantly from the spirit and intended scope of the present invention. Further, it should also be understood that although a rounded leading surface 24 for reinforced tip 22 is preferred, other tip configurations may be used such as conical, bullet-shaped, or the like which will have different, but viable leading surfaces 24. Additionally, when used in conjunction with a conventional dilator, tip 22 may have other types of tip configurations.

Moreover, it should also be understood that the guide 10 of the present invention need not be hollow. Of course, an elongate, cylindrical body 12 without a hollow interior 18 could not be used in conjunction with a conventional guide wire, but the use of a guide wire is not required for some insertion procedures.

The guide 10 of the present invention is particularly adapted for use in a simplified method for effecting femoral venous cannulation. Although it should be appreciated that guide 10 can be used to effect other types of cannulation (for example, femoral arterial or iliac cannulation), for the purposes of describing the present invention only femoral venous cannulation will be described. It is intended, however, that other types of cannulation are possible using the present invention and are expressly intended to be covered within the spirit and scope of the invention.

Figure 3:
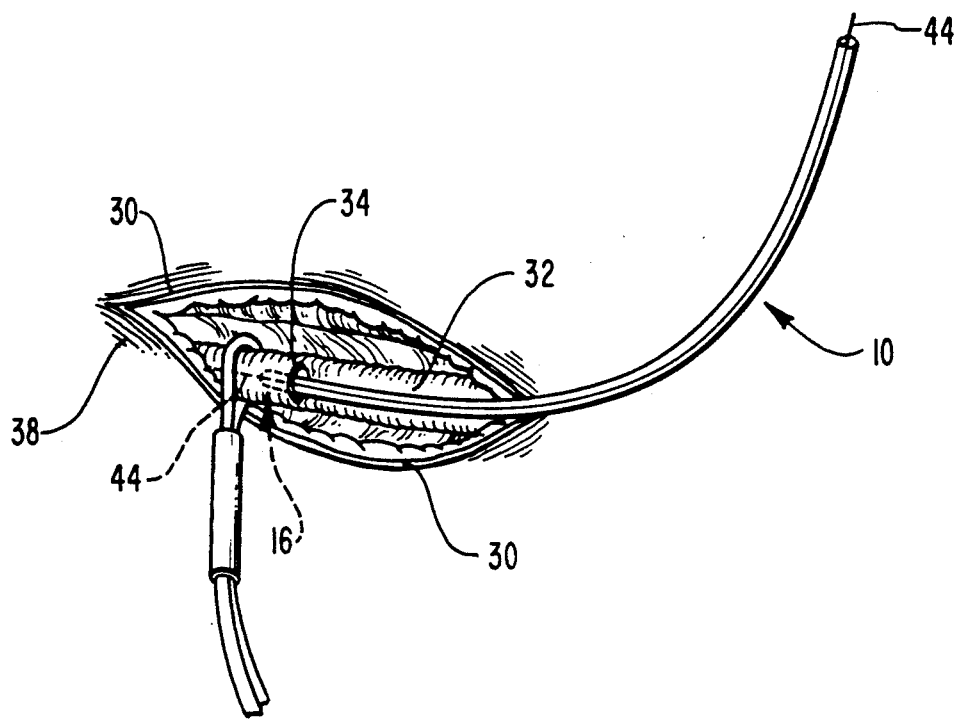
FIG. 3 is a perspective view of a femoral venotomy showing the guide of the present invention being inserted into the vein over a guide wire.
Figure 4:
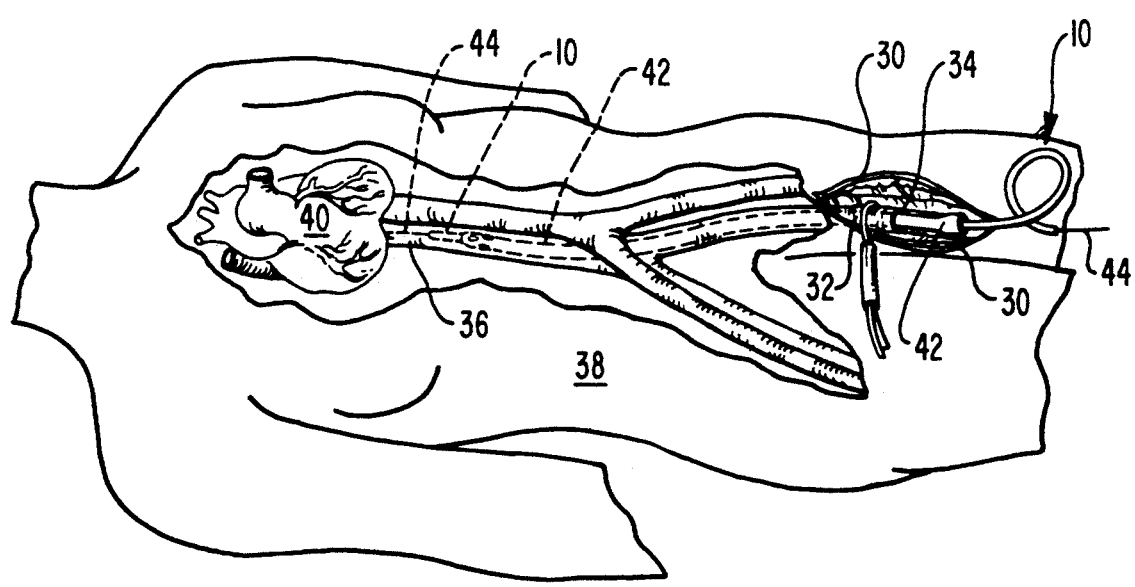
FIG. 4 is a perspective view of a patient with a portion of the torso shown in a cutaway view showing the insertion of a venous cannula into the inferior vena cava over a guide wire and the guide of the present invention.

As illustrated in FIG. 3, an incision 30 is made which exposes the femoral vessels and the common femoral vein 32. A venotomy (designated at 34) is made in the femoral vein 32 through which the guide 10 of the present invention may be inserted and then advanced. Advancement of the guide 10 through the femoral vein 32 into the inferior vena cava 36 of a patient 38 is illustrated in FIG. 4. Since guide 10 is soft and flexible, it can be easily manipulated into the inferior vena cava 36 and then, if desired, into the right atrium of a heart 40.

When so disposed within the venous system, the guide 10 provides a path over which the venous cannula 42, of a type such as the one shown in FIG. 5, can be threaded and advanced into the desired position in the right atrium of the heart 40. If difficulty is encountered during advancement of the venous cannula 42, table flexion at the hip is often a helpful maneuver. When the venous cannula 42 is disposed in its proper position, guide 10 may be removed so that the extracorporeal life support equipment (not shown) can be connected to the venous cannula 42.

In both FIGS. 3 and 4, a guide wire 44 is shown disposed within the guide 10 to illustrate how the guide 10 may be used with a guide wire 44. Like with the guide 10, after the venous cannula 42 is in place, the guide wire 44 may be removed to permit connection to the extracorporeal life support equipment.

Although both FIGS. 3 and 4 show the use of guide 10 in conjunction with a guide wire 44, it should be understood that the configuration of the guide 10 of the present invention is such that, in many instances a guide wire 44 will not be necessary to effect insertion and advancement of the guide 10 through the vessel. In such instances, it is preferred that the guide 10 be used without using a guide wire 44. Additionally, there are instances when the guide 10 of the present invention can best be used in conjunction with a conventional dilator (not shown), however, it should be appreciated that the guide 10 may be used with or without a dilator according to the particular needs of the patient 38 and the procedure used.

Turning now to FIGS. 5 and 6, illustrated are a venous cannula 42 (FIG. 5) and an arterial cannula 46 (FIG. 6) each of a type particularly suitable for use in connection with the guide 10 of the present invention. In FIG. 5 is a venous cannula 42 of basically known construction having a proximate end 48, an elongated, hollow body 50 with a wire reinforcement member 52, a plurality of drainage openings 54, and a distal end 56 with a tip 58 having a guide opening 60. In FIG. 6 is an arterial cannula 46 of basically known construction having a proximate end 62, an elongated, hollow body 64 with a wire reinforcement member 66, and a flow-through tip 68. An opening 70 of sufficient diameter to permit the passage therethrough of the guide 10 is provided in the flow-through tip 68. It is preferred that guide 10 accommodate venous cannulae 42 and/or arterial cannulae 46 having diameters in an approximate range of 26 to 36 French. However, larger or smaller diameter cannulae may be used in conjunction with a guide 10.

Of course, in view of the foregoing, a system for providing venous cannulation may comprise a guide 10 and a venous cannula 42, either with or without a guide wire 44. Likewise, a system for providing arterial cannulation may comprise a guide 10 and an arterial cannula 46, either with or without a guide wire 44. Such systems provide all the apparatus needed to effect venous or arterial cannulation in a safe and rapid manner.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method used for femoral venous cannulation of a patient, comprising the steps of:
   (a) exposing the femoral vessels;
   (b) making a venotomy in the common femoral vein;
   (c) inserting through the venotomy a guide comprising an elongate, flexible body having a hollow interior, a proximate end, and a distal end, said proximate end having an opening in communication with said hollow interior, said distal end having a reinforced tip with a rounded leading surface and a passageway therethrough, said passageway being in communication with said hollow interior and said passageway having a diameter slightly larger than the diameter of a conventional guide wire and smaller than the diameter of said hollow interior of said body;
   (d) advancing said reinforced tip of said guide to a desired position within the patient;
   (e) threading over said guide a venous cannula;
   (f) inserting through the venotomy said venous cannula while maintaining the disposition of said venous cannula over said guide;
   (g) advancing said venous cannula to the desired position within the patient.

2. A method as set forth in claim 1, further comprising the step of removing said guide from disposition within said venous cannula while maintaining said venous cannula in the desired position with the patient.

3. A method as set forth in claim 1, further comprising the steps of:
   inserting through the venotomy a guide wire;
   advancing the inserted end of said guide wire to the desired position within the patient; and
   threading over said guide wire said guide such that said guide wire passes through said opening, said hollow interior, and said passageway such that said guide is disposed over said guide wire.

4. A method as set forth in claim 3, further comprising the step of removing said guide wire from disposition within the patient while maintaining said venous cannula in the desired position within the patient.

5. Apparatus used for cannulation of a patient, comprising:
   a guide comprising an elongate, flexible body having a hollow interior, a proximate end, and a distal end, said proximate end having an opening in communication with said hollow interior, said distal end having a reinforced tip with a rounded leading surface and a passageway therethrough, said passageway being in communication with said hollow interior and said passageway having a diameter slightly larger than the diameter of a conventional guide wire and smaller than the diameter of said hollow interior of said body; and
   an elongate hollow cannula having a hollow interior space with a diameter sufficiently larger than the outer diameter of said guide for permitting passage of said guide therethrough.

6. Apparatus as set forth in claim 5; wherein said cannula is a venous cannula.

7. Apparatus as set forth in claim 5; wherein said cannula is an arterial cannula.

8. Apparatus used for cannulation of a patient, comprising:

a guide wire;

a guide comprising an elongate, flexible body having a hollow interior, a proximate end, and a distal end, said proximate end having an opening in communication with said hollow interior, said distal end having a reinforced tip with a rounded leading surface and a passageway therethrough, said passageway being in communication with said hollow interior and said passageway having a diameter only slightly larger than the diameter of the guide wire and smaller than the diameter of said hollow interior of said body; and an elongate hollow cannula having a hollow interior space with a diameter sufficiently larger than that of said guide for permitting passage of said guide therethrough.

9. Apparatus as set forth in claim 8, wherein said body is cylindrical and form maintaining.

10. Apparatus as set forth in claim 8, wherein said guide is constructed of flexible PVC.

11. Apparatus as set forth in claim 8, wherein said guide means has an outermost diameter in a range of approximately 10 to 20 French.

12. Apparatus as set forth in claim 8, wherein said guide is constructed to be visible by fluoroscopy.

13. Apparatus as set forth in claim 8, wherein said cannula is a venous cannula.

14. An apparatus as set forth in claim 8, wherein said cannula is an arterial cannula.

* * * * *